(12) United States Patent
Vitt et al.

(10) Patent No.: US 12,037,305 B2
(45) Date of Patent: Jul. 16, 2024

(54) CALCIUM SALT POLYMORPHS AS ANTI-INFLAMMATORY, IMMUNOMODULATORY AND ANTI-PROLIFERATIVE AGENTS

(71) Applicant: Immunic AG, Gräfelfing (DE)

(72) Inventors: Daniel Vitt, Germering (DE); Andreas Mühler, Munich (DE); Manfred Gröppel, Erlangen (DE); Hella Kohlhof, Munich (DE)

(73) Assignee: Immunic AG, Grafelfing (DE)

( * ) Notice: Subject to any disclaimer, the term of this patent is extended or adjusted under 35 U.S.C. 154(b) by 922 days.

(21) Appl. No.: 16/981,122

(22) PCT Filed: Mar. 15, 2019

(86) PCT No.: PCT/EP2019/056560
§ 371 (c)(1),
(2) Date: Sep. 15, 2020

(87) PCT Pub. No.: WO2019/175396
PCT Pub. Date: Sep. 19, 2019

(65) Prior Publication Data
US 2021/0017125 A1    Jan. 21, 2021

(30) Foreign Application Priority Data

Mar. 16, 2018  (EP) .................................. 18162244

(51) Int. Cl.
*C07C 233/60*    (2006.01)
(52) U.S. Cl.
CPC ........ *C07C 233/60* (2013.01); *C07B 2200/13* (2013.01)
(58) Field of Classification Search
CPC . C07C 233/60; C07B 2200/13; A61K 31/196; A61K 37/00
See application file for complete search history.

(56) References Cited

U.S. PATENT DOCUMENTS

| 8,653,138 B2 | 2/2014 | Ammendola et al. |
| 2012/0029034 A1 | 2/2012 | Ammendola et al. |
| 2012/0035175 A1 | 2/2012 | Ammendola et al. |

FOREIGN PATENT DOCUMENTS

| WO | WO 03/006425 A2 | 1/2003 | |
| WO | WO 2004/056797 | 7/2004 | |
| WO | 2012/001148 A1 | 1/2012 | |
| WO | WO-2012001148 A1 * | 1/2012 | ................ A61P 1/00 |
| WO | WO-2015169944 A1 * | 11/2015 | ........... A61K 31/196 |
| WO | WO-2017117372 A1 * | 7/2017 | ........... A61K 31/167 |

OTHER PUBLICATIONS

Reis et al. Archives of Biochemistry and Biophysics 632, 2017, 175-191 (Year: 2017).*
Kulkarni. AJP, Jun. 2010, vol. 176, No. 6 (Year: 2010).*
Rusai. Transplantation, vol. 93, No. 11, 2012 (Year: 2012).*
Herrlinger. Efficacy, safety, and tolerability of videofludimus in patients with inflammatory bowel disease: the entrance study. Gastroenterology, 2011; 140:S588-S589 (Year: 2011).*
International Search Report dated May 14, 2019 issued in corresponding PCT/EP2019/056560 application (3 pages).
Cairo, Mino R. et al., "Crystalline Polymorphism of Organic Compounds," Topics in Current Chemistry, vol. 198, Sec. 3.1, pp. 163-208 (1998).

* cited by examiner

*Primary Examiner* — Susanna Moore
*Assistant Examiner* — Luisalberto Gonzalez
(74) *Attorney, Agent, or Firm* — FINNEGAN, HENDERSON, FARABOW, GARRETT & DUNNER, LLP

(57) ABSTRACT

Subject matter of the present invention is a white crystalline polymorph A of the Ca salt of a compound according to formula I or a solvate and/or a hydrate thereof with a molar ratio of a compound according to formula I or a solvate and/or a hydrate thereof to calcium which is 2±0.3. Subject matter of the present invention is in particular a compound according to formula I or a solvate and/or a hydrate thereof which is characterized by an X-ray powder diffraction pattern having characteristic peaks expressed in degrees 2theta at ±0.2 of the values shown below: 2 theta=5.91°, 9.64°, 16.78°, 17.81°, 19.81°, 25.41° In particular the invention refers to new polymorphs of calcium salts of the Ca salt of a compound according to formula I or a solvate and/or a hydrate thereof which inhibits dihydroorotate dehydrogenase (DHODH), a process for their manufacture, pharmaceutical compositions containing them and to their use for the treatment and prevention of diseases, in particular their use in diseases where there is an advantage in inhibiting dihydroorotate dehydrogenase (DHODH).

16 Claims, 6 Drawing Sheets

Figure 1:
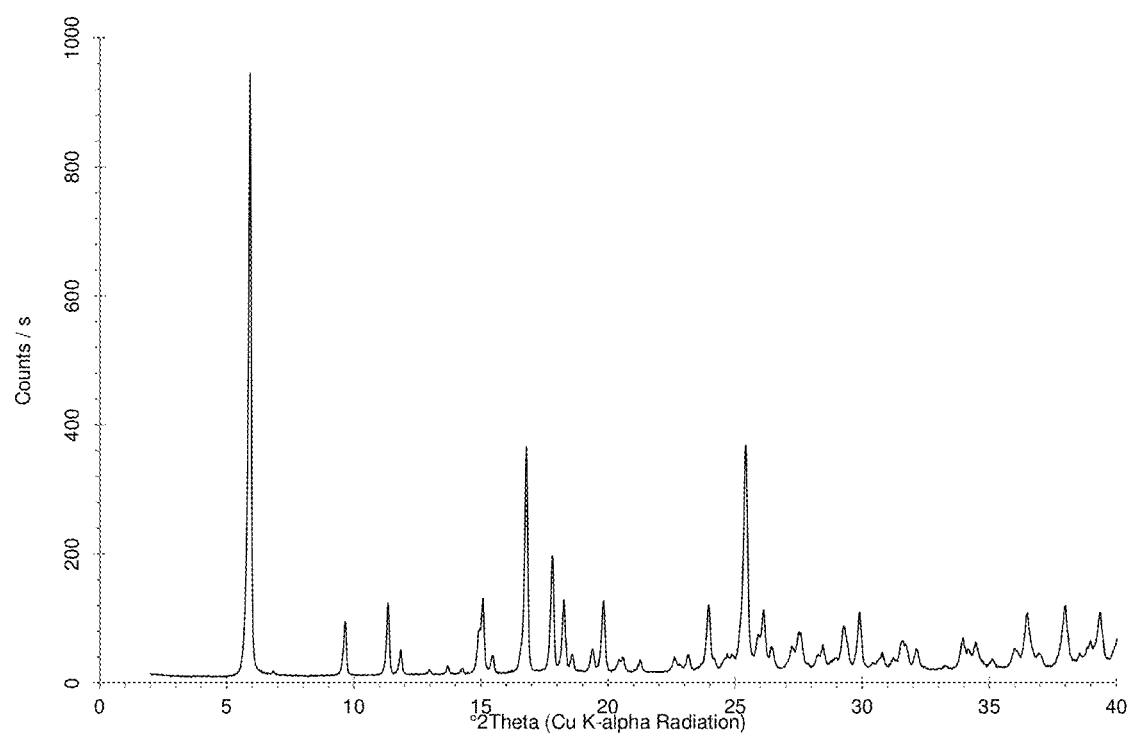

CALCIUM SALT POLYMORPHS AS ANTI-INFLAMMATORY, IMMUNOMODULATORY AND ANTI-PROLIFERATIVE AGENTS

Subject matter of the present invention is a white crystalline polymorph A of the Ca salt of a compound according to formula I or a solvate and/or a hydrate thereof with a molar ratio of a compound according to formula I or a solvate and/or a hydrate thereof to calcium which is 2±0.3. Subject matter of the present invention is in particular a compound according to formula I or a solvate and/or a hydrate thereof which is characterized by an X-ray powder diffraction pattern having characteristic peaks expressed in degrees 2theta at ±0.2 of the values shown below: 2 theta=5.91°, 9.64°, 16.78°, 17.81°, 19.81°, 25.41° In particular the invention refers to new polymorphs of calcium salts of a compound according to formula I or a solvate and/or a hydrate thereof which inhibits dihydroorotate dehydrogenase (DHODH), a process for their manufacture, pharmaceutical compositions containing them and to their use for the treatment and prevention of diseases, in particular their use in diseases where there is an advantage in inhibiting dihydroorotate dehydrogenase (DHODH). Examples of relevant diseases are given below.

Inflammatory Bowel Disease (IBD) is a group of inflammatory conditions of the colon and small intestine. With Crohn's Disease and Ulcerative Colitis as principal types thereof. Crohn's disease can affect the small intestine and large intestine, as well as the mouth, esophagus, stomach and the anus. Ulcerative colitis primarily affects the colon and the rectum.

Rheumatoid arthritis (RA) is a disease that is quite common especially among elder people. Its treatment with usual medications as for example non-steroid anti-inflammatory agents is not satisfactory. In view of the increasing ageing of the population, especially in the developed Western countries or in Japan the development of new medications for the treatment of RA is urgently required.

WO 2003/006425 describes certain specific compounds, which are reported to be useful for treatment and prevention of diseases where there is an advantage in inhibiting dihydroorotate dehydrogenase (DHODH). However, the specific salts according to the present invention are not disclosed. WO 2012/001148 describes the calcium salts of said compounds. However, the specific polymorphs according to the present invention are not disclosed.

WO 99/38846 and EP 0 646 578 disclose compounds which are reported to be useful for treatment of RA.

A medicament against rheumatoid arthritis with a new mechanism of action, leflunomide, was put on the market by the company Aventis under the tradename ARAVA [EP 780128, WO 97/34600]. Leflunomide has immunomodulatory as well as anti-inflammatory properties [EP 217206, DE 2524929]. The mechanism of action is based upon the inhibition of dihydroorotate dehydrogenase (DHODH), an enzyme of the pyrimidine biosynthesis.

De Julian-Ortiz (J. Med. Chem. 1999, 42, 3308-3314) describes certain potential Anti-Herpes compounds with cyclopentenoic acid moieties.

DE 33 46 814 A1 describes certain carbonic acid amide derivatives for the treatment, prevention and amelioration of diseases connected to cerebral dysfunction and symptoms caused thereby.

In the human body, DHODH catalyzes the synthesis of pyrimidines, which are in particular necessary for cellular metabolism. An inhibition of DHODH leads to block of transcription of sensitive genes in metabolically activated cells, whereas cells with normal metabolic activity obtain their required pyrimidine building blocks from the pyrimidine salvage pathway and show normal transcriptional activity. Disease relevant activated lymphocytes rely on de novo pyrimidine syntheses and react particularly sensitively to DHODH inhibition. Some substances that inhibit DHODH are important medicaments for the treatment of chronic inflammatory and auto-immune diseases.

A compound named leflunomide (ARAVA) has been the first approved inhibitor of DHODH and is used for the treatment of human diseases, in particular rheumatoid arthritis. WO 99/45926 is a further reference that discloses compounds which act as inhibitors of DHODH. Another drug which is targeting DHODH is teriflunomide (AUBAGIO®) is the metabolite of leflunomide. Teriflunomide is approved for the treatment of multiple sclerosis in some countries.

JP-A-50-121428 discloses N-substituted cyclopentene-1,2-dicarboxylic acid monoamides as herbicides and their syntheses. For example, N-(4-chlorophenyl)-1-cyclopentene-1,2-dicarboxylic acid monoamide is produced by reacting 1-cyclopentene-1,2-dicarboxylic anhydride with 4-chloroaniline.

In the Journal of Med. Chemistry, 1999, Vol. 42, pages 3308-3314, virtual combinatorial syntheses and computational screening of new potential Anti-Herpes compounds are described. In Table 3 on page 3313 experimental results regarding $IC_{50}$ and cytotoxicity are presented for 2-(2,3-difluorophenylcarbamoyl)-1-cyclopentene-1-carboxylic acid, 2-(2,6-difluorophenylcarbamoyl)-1-cyclopentene-1-carboxylic acid and 2-(2,3,4-trifluorophenyl-carbamoyl)-1-cyclopentene-1-carboxylic acid.

DE 3346814 and U.S. Pat. No. 4,661,630 disclose carboxylic acid amides. These compounds are useful for diseases attended with cerebral dysfunction and also have anti-ulcer, anti-asthma, anti-inflammatory and hypo-cholesterol activities.

In EP 0097056, JP 55157547, DE 2851379 and DE 2921002 tetrahydrophthalamic acid derivatives are described.

It is an object of the present invention to provide effective agents, specifically in the form of certain polymorphs of their calcium salts, which can be used for the treatment of diseases which require the inhibition of DHODH.

It was also an object of the present invention to provide compounds that inhibit DHODH in a range similar to the compounds disclosed in WO2003/006425 and WO 2012/001148 and at the same time show a white colour in order to facilitate double blind placebo controlled clinical studies.

It was also an object of the present invention to provide compounds and composition comprising that compounds that inhibit DHODH in a range similar to the compounds disclosed in WO2003/006425 and WO 2012/001148 and are characterized by having a THF content below 720 ppm in order to be in compliance with guidelines of the European Medicines Agency (e.g. with the version 6 Dec. 2016; EMA/CHMP/ICH/82260/2006)

Particularly, it has previously been found that certain compounds of the general formula (I) shown herein below, such as 2-(3-Fluoro-3'-methoxy-biphenyl-4-ylcarbamoyl)-cyclopent-1-enecarboxylic acid (INN Vidofludimus), exhibit good anti-inflammatory activity and their usability in the oral therapy for the treatment of autoimmune diseases such as for example rheumatoid arthritis or inflammatory bowel diseases had been addressed.

Accordingly, a novel white polymorph of Calcium-vidofludimus named polymorph A with an inhibitory effect on DHODH, in particular human DHODH, was provided. Furthermore, a composition was provided comprising said white polymorph of Calcium-vidofludimus named polymorph A characterized by having a Tetrahydroduran (THF) content below 720 ppm.

The invention refers to a white crystalline calcium salt of 2-({3-fluoro-3'-methoxy-[1,1'-biphenyl]-4-yl}carbamoyl) cyclopent-1-ene-1-carboxylic acid) according to formula (I) or a solvate and/or a hydrate thereof, CAS-No 717824-30-1

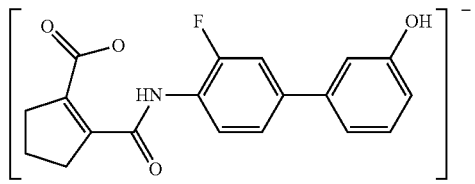

Thus, subject matter of the present invention is a white crystalline calcium salt of vidofludimus with a molar ratio of vidofludimus to calcium is 2±0.3 or a solvate and/or a hydrate thereof. In contrast to the pale yellow polymorph as described in EP 2588446B1, e.g. example 4, subject matter of the present invention is of white color.

White crystal can be defined as crystals with pure white color similar to the RAL color code RAL9010 that is equal or similar to the US Federal Standard 595 color code "White 506", #27885.

A solvate for all embodiments of the invention maybe selected from the group comprising ethanol, propanol, isopropanol, butanol, THF, water. In a preferred embodiment for all embodiments of the invention the solvate is a hydrate. In one preferred embodiment the solvate is a calcium dihydrate for all embodiments of the invention.

In particular, subject matter of the present invention is a white crystalline polymorph A of the Ca salt of a compound according to formula I (vidofludimus) or a solvate and/or a hydrate thereof thereof which is characterized by an X-ray powder diffraction pattern having characteristic peaks expressed in degrees 2theta at ±0.2 of the values shown below:

2 theta=5.91°, 9.64°, 16.78°, 17.81°, 19.81°, 25.41°

In a particular embodiment, subject matter of the present invention is a white crystalline polymorph A of the Ca salt of a compound according to formula I (vidofludimus) (Calcium-vidofludimus) or a solvate and/or a hydrate thereof wherein the characteristic peaks which have 2theta at ±0.2 of the values shown below:

All 2 theta values mentioned in this application relate to a wave length of X-Ray radiation from a source that is Copper Kalpha. Thus, the 2 theta values are obtained with a radiation wave length: Cu K-alpha; 0.15418 nm.

TABLE 1

Peak-list of Calcium-vidofludimus polymorph A

| Angle 2-Theta ° | d value Angstrom | Intensity |
| --- | --- | --- |
| 5.91 | 14.95 | vs |
| 6.83 | 12.93 | vw |
| 9.64 | 9.17 | w |
| 11.33 | 7.80 | w |

TABLE 1-continued

Peak-list of Calcium-vidofludimus polymorph A

| Angle 2-Theta ° | d value Angstrom | Intensity |
| --- | --- | --- |
| 11.82 | 7.48 | w |
| 12.98 | 6.81 | vw |
| 13.70 | 6.46 | vw |
| 14.27 | 6.20 | vw |
| 15.04 | 5.89 | w |
| 15.44 | 5.73 | vw |
| 16.78 | 5.28 | s |
| 17.81 | 4.98 | m |
| 18.25 | 4.86 | w |
| 18.58 | 4.77 | vw |
| 19.39 | 4.57 | w |
| 19.81 | 4.48 | w |
| 20.53 | 4.32 | vw |
| 21.26 | 4.18 | vw |
| 22.63 | 3.93 | vw |
| 23.16 | 3.84 | vw |
| 23.96 | 3.71 | w |
| 24.73 | 3.60 | vw |
| 25.41 | 3.50 | s |
| 26.12 | 3.41 | w |
| 26.44 | 3.37 | w |
| 27.25 | 3.27 | w |
| 27.55 | 3.24 | w |
| 28.45 | 3.13 | w |
| 28.91 | 3.09 | vw |
| 29.29 | 3.05 | w |
| 29.89 | 2.99 | w |
| 30.77 | 2.90 | w |
| 31.22 | 2.86 | vw |
| 31.60 | 2.83 | w |
| 32.13 | 2.78 | w |
| 33.25 | 2.69 | vw |
| 33.98 | 2.64 | w |
| 34.48 | 2.60 | w |
| 35.12 | 2.55 | vw |

In a particular embodiment, subject matter of the present invention is a white crystalline polymorph A of Calcium-vidofludimus or a solvate and/or a hydrate thereof characterized by the x-ray powder diffraction pattern shown in FIG. 1.

Figure 2:
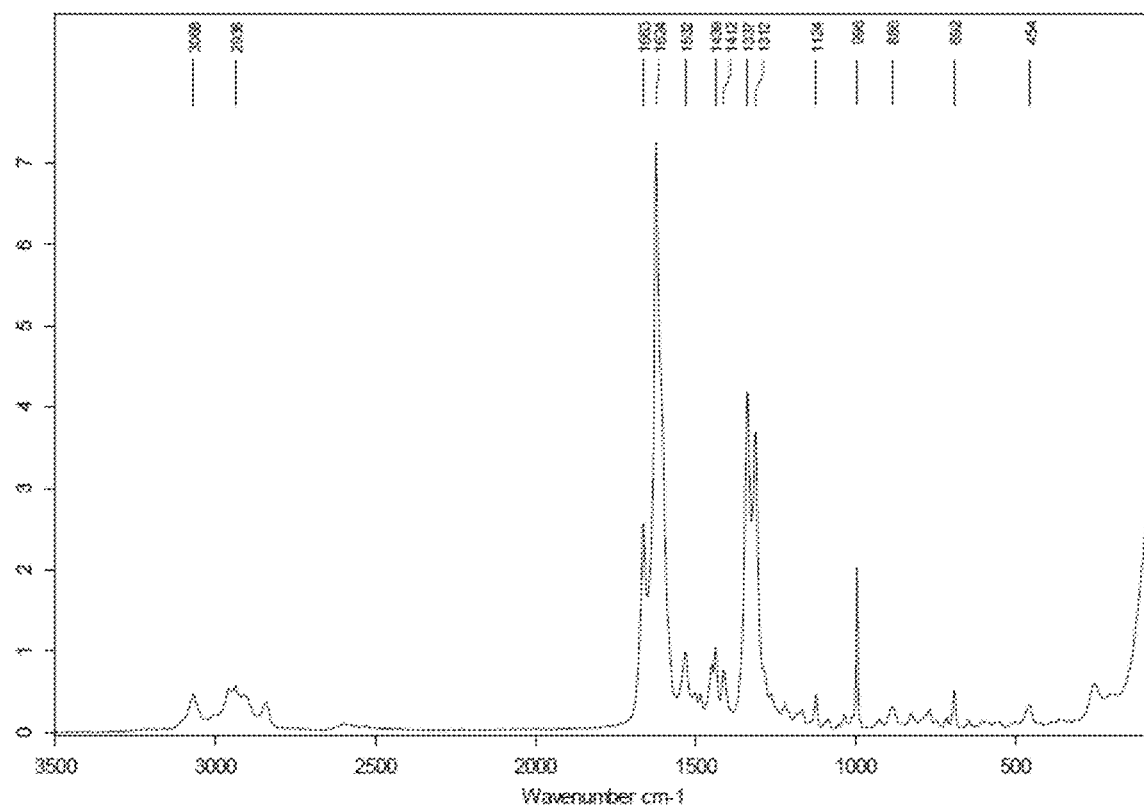

In a particular embodiment, subject matter of the present invention is a white crystalline polymorph A of Calcium-vidofludimus or a solvate and/or a hydrate thereof that is characterized by an FT Raman absorption spectrum having the following characteristic peaks expressed in $cm^{-1}$ 1664, 1624, 1617, 1532, 1449, 1338 the spectrum is shown in FIG. 2.

In a particular embodiment, subject matter of the present invention is a white crystalline polymorph A of Calcium-vidofludimus or a solvate and/or a hydrate thereof which is characterized by an IR absorption spectrum having characteristic peaks expressed in $cm^{-1}$ 1980, 1659, 1584, 1335, 1145, the spectrum is shown in FIG. 3.

Figure 4:
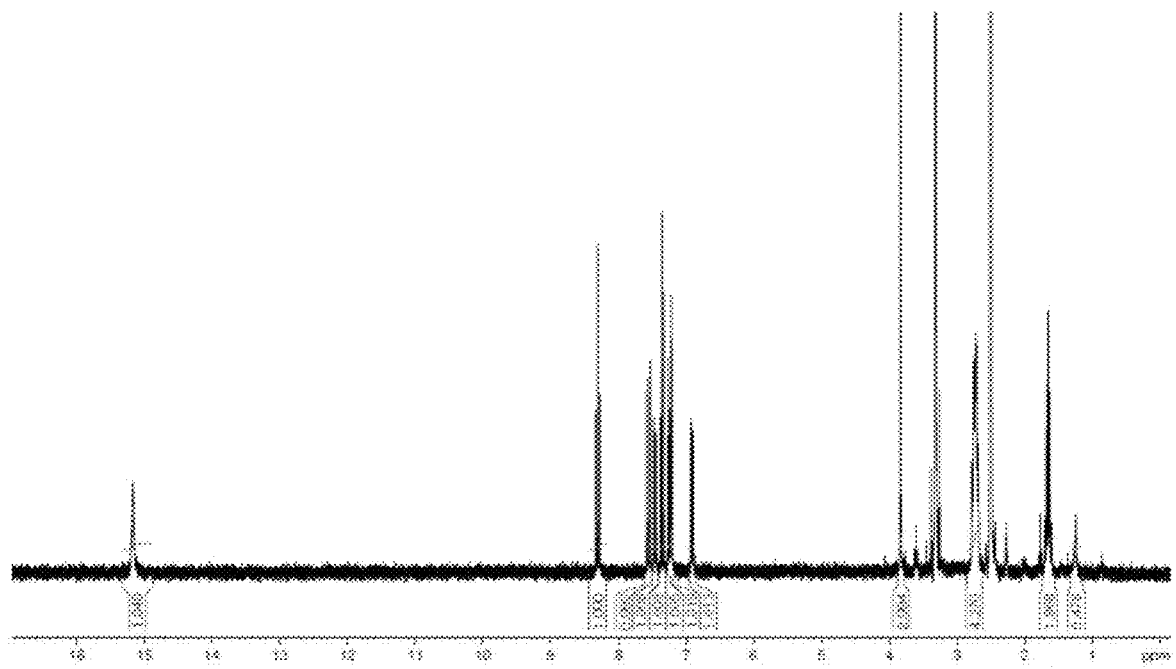

In a particular embodiment, subject matter of the present invention is a white crystalline polymorph A of Calcium-vidofludimus or a solvate and/or a hydrate thereof wherein which is characterized by an $^1$H-NMR spectrum having characteristic peaks expressed in ppm, 15.2, 8.3, 7.6, 7.5, 7.4, 7.2, 6.8, 3.8, 2.7, 1.6. The spectrum is shown in FIG. 4.

In a particular embodiment, subject matter of the present invention is a white crystalline polymorph A of Calcium-vidofludimus or a solvate and/or a hydrate thereof wherein which is a hydrate with a molar ratio of vidofludimus to water of about 1:1.

In a particular embodiment, subject matter of the present invention is a pharmaceutical formulation comprising a white crystalline polymorph A of Calcium-vidofludimus thereof or obtainable from a Ca-Vidofludimus or a solvate and/or a hydrate thereof, preferable obtainable from a crystalline polymorph of the Ca salt of vidofludimus or a solvate and/or a hydrate thereof, e.g. obtainable from a crystalline polymorph B of the Ca salt of vidofludimus or a solvate and/or a hydrate thereof in a process as described below in more detail.

This is the first time that it was possible to provide a pharmaceutical formulation or composition comprising a polymorph of Ca salt of vidofludimus that contained less than 720 ppm THF. Thus, in a particular embodiment, subject matter of the present invention is a pharmaceutical formulation or a composition comprising a polymorph of vidofludimus having a THF content of less than 720 ppm THF, preferably less than 650 ppm, preferably less than 600 ppm, preferably less than 500 ppm, preferably less than 400 ppm, preferably less than 300 ppm, preferably less than 250 ppm, preferably less than 200 ppm, preferably less than 100 ppm.

In a specific embodiment, subject matter of the present invention is a pharmaceutical formulation comprising a white crystalline polymorph A of Calcium-vidofludimus thereof or a solvate/and or hydrate thereof obtainable from a Ca-Vidofludimus or a solvate and/or a hydrate thereof, preferable obtainable from a crystalline polymorph of the Ca salt of vidofludimus or a solvate and/or a hydrate thereof, e.g. obtainable from a crystalline polymorph B of the Ca salt of vidofludimus or a solvate and/or a hydrate thereof in a process as described below in more detail, wherein said pharmaceutical formulation is having a THF content of less than 720 ppm, preferably less than 650 ppm, preferably less than 600 ppm, preferably less than 500 ppm, preferably less than 400 ppm, preferably less than 300 ppm, preferably less than 250 ppm, preferably less than 200 ppm, preferably less than 100 ppm.

Subject matter of the present invention is the white crystalline polymorph A of Calcium-vidofludimus thereof according to the present invention or a pharmaceutical formulation according to the present invention for use as a medicament.

Subject matter of the present invention is the crystalline polymorph A of Calcium-vidofludimus or a solvate and/or a hydrate thereof according to the present invention or a pharmaceutical formulation according to the present invention for use as in the treatment of a disease selected from the group comprising rheumatism, acute immunological disorders, autoimmune diseases, diseases caused by malignant cell proliferation, inflammatory diseases, diseases that are caused by protozoal infestations in humans and animals, diseases that are caused by viral infections and Pneumocystis carinii, fibrosis, uveitis, rhinitis, asthma or athropathy.

Subject matter of the present invention is the crystalline polymorph A of Calcium-vidofludimus or a solvate and/or a hydrate thereof according to the present invention or a pharmaceutical formulation according to the present invention for use as in the treatment of a disease selected from the group comprising wherein the disease or a therapeutic indication is selected from the group comprising graft versus host and host versus graft reactions, rheumatoid arthritis, psoriatic arthritis, multiple sclerosis, amyotrophic lateral sclerosis, lupus erythematosus, lupus nephritis, inflammatory bowel disease, type 1 diabetes, autoimmune hepatitis, primary scleroting cholangitis, primary biliary cholangitis and psoriasis. In one particular embodiment of the invention said patient suffers from inflammatory bowel disease, in particular ulcerative colitis and Crohn's disease.

Subject matter of the present invention is a process for the manufacture of white crystalline polymorph A of Calcium-vidofludimus or a solvate and/or a hydrate thereof as defined in any of the embodiments above, wherein said process is a slurry-to-slurry process starting from Ca-vidofludimus or a solvate and/or a hydrate thereof, preferable obtainable from a crystalline polymorph of the Ca salt of vidofludimus or a solvate and/or a hydrate thereof wherein said process comprises the steps of:

washing the calcium salt vidofludimus or a solvate and/or a hydrate thereof with the an aprotic organic solvent preferably selected from the group comprising DMF, DMSO, NMP, THF, Acetone, Dioxane, 2-Methyl-THF or (Methanol/CH2Cl2 (1:3)), preferably acetone, and slurring the isolated Calcium-vidofludimus or a solvate and/or a hydrate thereof obtained in an alcoholic solvent and adding water to the slurry.

With the inventive process is it possible to transform a Ca-Vidofludimus or a solvate and/or a hydrate thereof, preferably a crystalline polymorph of the Ca salt of vidofludimus or a solvate and/or a hydrate thereof, e.g. a crystalline polymorph B of the Ca salt of vidofludimus or a solvate and/or a hydrate thereof into a white crystalline polymorph A of Calcium-vidofludimus or a solvate and/or a hydrate thereof, having a THF content of less than 720 ppm.

Subject matter of the present invention is a process for the manufacture of white crystalline polymorph A of Calcium-vidofludimus or a solvate and/or a hydrate thereof as defined in any of the embodiments above, which process comprises the steps of
a) adding to a mixture of calcium hydroxide and free acid of vidofludimus an organic solvent and water
b) adding an aprotic organic solvent, fully mixable with water to said suspension of Calcium-vidofludimus or a solvate and/or a hydrate thereof obtained in step a)
c) recovering the salt of Calcium-vidofludimus or a solvate and/or a hydrate thereof from the mixture obtained in step b), and
d) washing the calcium salt of Calcium-vidofludimus or a solvate and/or a hydrate thereof obtained in step c) with the aprotic organic solvent mentioned in step b).
e) slurring the isolated of Calcium-vidofludimus or a solvate and/or a hydrate thereof obtained in step d) in an alcoholic solvent at 1580° C. in order to obtain Calcium-vidofludimus polymorph B.
f) adding water to the slurry obtained in step e) at 15-85° C. in order to obtain Calcium-vidofludimus polymorph A or a solvate and/or a hydrate thereof again with a reduced amount of aprotic organic solvent.

The organic solvent according to step a) maybe selected from the group comprising THF, 2-Methyl-THF, Dioxane or similar solvents.

The evaporation according to step c) maybe be achieved by distilling off the organic solvent used in a by vacuum distillation or distillation at normal pressure.

An aprotic organic solvent maybe selected from the group comprising DMF, DMSO, NMP, THF, Acetone, Dioxane, 2-Methyl-THF or (Methanol/CH2Cl2 (1:3)).

A suspension/slurry is the mixture of crystalline, solid product in the mixture of solvents utilized. Visual inspection is used when determining whether a slurry or suspension or whether a solution is obtained.

The recovering of the calcium salt of vidofludimus (4SC-101, SC12267) or a solvate and/or a hydrate thereof from the mixture obtained in step e), maybe achieved as follows: Isolation of the product by any kind of solid/liquid separation as filtration, centrifugation or similar.

The alcoholic solvent according to step e) maybe selected from the group comprising Methanol, Ethanol or i-Propanol In one embodiment the recovering of the calcium salt of vidofludimus (4SC-101, SC12267) or a solvate and/or a hydrate thereof from the mixture obtained in step e), maybe achieved as follows: Isolation of the product by any kind of solid/liquid separation as filtration, centrifugation or similar.

In a particular embodiment subject matter of the invention is a process for the manufacture of a crystalline polymorph according to process as described above wherein after step f) a drying step is added, and optionally subsequently a milling step and optionally subsequently a recrystallization step is added.

In another particular embodiment subject matter of the invention is a process for the manufacture of a crystalline polymorph according to process as described above wherein after step b) and before step c) the solution is filtered and then the filter is washed with said organic solvent.

In another particular embodiment subject matter of the invention is a process for the manufacture of a crystalline polymorph according to process as described above wherein the suspension of step a) is heated to 25-30° C.

In another particular embodiment subject matter of the invention is a process for the manufacture of a crystalline polymorph according to process as described above wherein the suspension of step e) is heated to 15-25° C.

In another particular embodiment subject matter of the invention is a process for the manufacture of a crystalline polymorph according to process as described above wherein said organic solvent is THF.

In another particular embodiment subject matter of the invention is a process for the manufacture of a crystalline polymorph according to process as described above wherein said aprotic organic solvent is acetone. In another particular embodiment subject matter of the invention is a process for the manufacture of a crystalline polymorph according to process as described above wherein said alcoholic solvent is preferably ethanol.

In another particular embodiment subject matter of the invention is a crystalline calcium salt of vidofludimus (4SC-101, SC12267) with a molar ratio of vidofludimus to calcium is 2±0.3 obtainable by a process as described above.

The polymorphs according to the present invention can be administered to animals, particularly to mammals, and in particular to humans, dogs and chickens as therapeutics per se, as mixtures with one another or in the form of pharmaceutical preparations which allow enteral or parenteral use and which as active constituent contain an effective dose of at least one of the aforementioned polymorphs of the invention, in addition to customary pharmaceutically innocuous excipients and additives.

The therapeutics can be administered orally, e.g. in the form of pills, tablets, coated tablets, sugar coated tablets, hard and soft gelatin capsules, solutions, syrups, emulsions or suspensions or as aerosol mixtures. Administration, however, can also be carried out rectally, e.g. in the form of suppositories, or parenterally, e.g. in the form of injections or infusions, or percutaneously, e.g. in the form of ointments, creams or tinctures.

For clinical trials it is an enormous advantage if the formulation comprising the active compound has a white color. Clinical trials are often double blinded to avoid "placebo-effects", i.e. to avoid a bias if either the physician or the patient may be able to recognize the placebo. The resulting inadequacy can lead to trial delayed and increased costs. Mandy Wan et al. *Arch Dis* Child September 2013, Vol 98 No. 9. Thus, if the composition comprising the active ingredient is colored measures have to be taken to equalize placebo and active formulation. Thus, it is an enormous advantage if the clinical formulation is white.

In addition to the aforementioned polymorphs of the invention, the pharmaceutical composition can contain further customary, usually inert carrier materials or excipients. Thus, the pharmaceutical preparations can also contain additives, such as, for example, fillers, extenders, disintegrants, binders, glidants, wetting agents, stabilizers, emulsifiers, preservatives, sweetening agents, colorants, flavorings or aromatizers, buffer substances, and furthermore solvents or solubilizers or agents for achieving a depot effect, as well as salts for changing the osmotic pressure, coating agents or antioxidants. They can also contain the aforementioned salts of two or more polymorphs of the invention and also other therapeutically active substances.

Thus, the polymorphs of the invention can be used alone or in combination with other active compounds for example with medicaments already known for the treatment of the aforementioned diseases, whereby in the latter case a favorable additive, amplifying effect is noticed. Suitable amounts to be administered to humans range from 5 to 500 mg, in particular 10 mg to 100 mg.

To prepare the pharmaceutical preparations, pharmaceutically inert inorganic or organic excipients can be used. To prepare pills, tablets, coated tablets and hard gelatin capsules, for example, lactose, corn starch or derivatives thereof, talc, stearic acid or its salts, etc. can be used. Excipients for soft gelatin capsules and suppositories are, for example, fats, waxes, semi-solid and liquid polyols, natural or hardened oils etc. Suitable excipients for the production of solutions and syrups are, for example, water, sucrose, invert sugar, glucose, polyols etc. Suitable excipients for the production of injection solutions are, for example, water, alcohols, glycerol, polyols or vegetable oils.

The dose can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 1 to 100 mg/kg animal body weight particularly 1 to 50 mg/kg. Suitable dosage rates for larger mammals, for example humans, are of the order of from about 10 mg to 3 g/day, conveniently administered once or in divided doses, e.g. 2 to 4 times a day, or in sustained release form.

In general, a daily dose of approximately 10 mg to 100 mg, particularly 10 to 50 mg, per human individual is appropriate in the case of the oral administration. In the case of other administration forms too, the daily dose is in similar ranges.

Embodiments of the invention are:
1. A white crystalline polymorph A of the Ca salt of a compound according to formula I or a solvate and/or a hydrate thereof

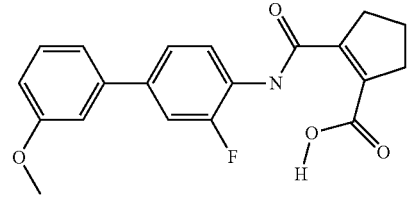

Formula I with a molar ratio of said compound according to formula I to calcium 2±0.3.

2. A white crystalline polymorph A of the Ca salt of a compound according to formula I or a solvate and/or a hydrate thereof according to embodiment 1 which is characterized by an X-ray powder diffraction pattern having characteristic peaks expressed in degrees 2theta at ±0.2 of the values shown below: 2 theta=5.91°, 9.64°, 16.78°, 17.81°, 19.81°, 25.41°

3. A white crystalline polymorph A of the Ca salt of a compound according to formula I or a solvate and/or a hydrate thereof according to embodiment 1 or 2, wherein the characteristic peaks which have 2theta at ±0.2 of the values shown below:

TABLE 1

Peak-list of Polymorph A of Ca salt of vidofludimus

| Angle 2-Theta ° | d value Angstrom | Intensity |
| --- | --- | --- |
| 5.91 | 14.95 | vs |
| 6.83 | 12.93 | vw |
| 9.64 | 9.17 | w |
| 11.33 | 7.80 | w |
| 11.82 | 7.48 | w |
| 12.98 | 6.81 | vw |
| 13.70 | 6.46 | vw |
| 14.27 | 6.20 | vw |
| 15.04 | 5.89 | w |
| 15.44 | 5.73 | vw |
| 16.78 | 5.28 | s |
| 17.81 | 4.98 | m |
| 18.25 | 4.86 | w |
| 18.58 | 4.77 | vw |
| 19.39 | 4.57 | w |
| 19.81 | 4.48 | w |
| 20.53 | 4.32 | vw |
| 21.26 | 4.18 | vw |
| 22.63 | 3.93 | vw |
| 23.16 | 3.84 | vw |
| 23.96 | 3.71 | w |
| 24.73 | 3.60 | vw |
| 25.41 | 3.50 | s |
| 26.12 | 3.41 | w |
| 26.44 | 3.37 | w |
| 27.25 | 3.27 | w |
| 27.55 | 3.24 | w |
| 28.45 | 3.13 | w |
| 28.91 | 3.09 | vw |
| 29.29 | 3.05 | w |
| 29.89 | 2.99 | w |
| 30.77 | 2.90 | w |
| 31.22 | 2.86 | vw |
| 31.60 | 2.83 | w |
| 32.13 | 2.78 | w |
| 33.25 | 2.69 | vw |
| 33.98 | 2.64 | w |
| 34.48 | 2.60 | w |
| 35.12 | 2.55 | vw |

4. A white crystalline polymorph A of the Ca salt of a compound according to formula I or a solvate and/or a hydrate thereof according to embodiment 1 or 2, characterized by the x-ray powder diffraction pattern shown in FIG. 1.

5. A white crystalline polymorph A of the Ca salt of a compound according to formula I or a solvate and/or a hydrate thereof according to any of embodiments 1 to 4 which is characterized by an FT Raman absorption spectrum having the following characteristic peaks expressed in cm$^{-1}$ 1664, 1624, 1617, 1532, 1449, 1338 the spectrum is shown in FIG. 2.

6. A white crystalline polymorph A of the Ca salt of a compound according to formula I or a solvate and/or a hydrate thereof according to any of embodiments 1 to 5 which is characterized by an IR absorption spectrum having characteristic peaks expressed in cm$^{-1}$ 1980, 1659, 1584, 1335, 1145, the spectrum is shown in FIG. 3.

7. A white crystalline polymorph A of the Ca salt of a compound according to formula I or a solvate and/or a hydrate thereof according to any of embodiments 1 to 6 which is characterized by an $^1$H-NMR spectrum having characteristic peaks expressed in ppm, 15.2, 8.3, 7.6, 7.5, 7.4, 7.2, 6.8, 3.8, 2.7, 1.6. The spectrum is shown in FIG. 4.

FIG. 4: $^1$H-NMR spectrum of Polymorph A of Ca vidofludimus

8. A white crystalline polymorph A of the Ca salt of a compound according to formula I or a solvate and/or a hydrate thereof according to any of embodiments 1 to 8 which is a hydrate with a molar ratio of a compound according to formula I to water of about 1:1.

9. A pharmaceutical formulation comprising a white crystalline polymorph A of the Ca salt of a compound according to formula I or a solvate and/or a hydrate thereof according to any of embodiments 1 to 8.

10. A pharmaceutical formulation according to embodiment 1 having a THF content of less than 720 ppm.

11. A white crystalline polymorph A of the Ca salt of a compound according to formula I or a solvate and/or a hydrate thereof according to any of embodiments 1 to 8 or a pharmaceutical formulation according to embodiment 9 or 10 for use as a medicament.

12. A white crystalline polymorph A of the Ca salt of a compound according to formula I or a solvate and/or a hydrate thereof according to any of embodiments 1 to 8 or a pharmaceutical formulation according to embodiment 9 or 10 for use as in the treatment of a disease selected from the group comprising rheumatism, acute immunological disorders, autoimmune diseases, diseases caused by malignant cell proliferation, inflammatory diseases, diseases that are caused by protozoal infestations in humans and animals, diseases that are caused by viral infections and Pneumocystis carinii, fibrosis, uveitis, rhinitis, asthma or athropathy.

13. A white crystalline polymorph A of the Ca salt of a compound according to formula I or a solvate and/or a hydrate thereof according to any of embodiments 1 to 8 or a pharmaceutical formulation according to embodiment 9 or 10 for use as in the treatment of a disease selected from the group comprising wherein the disease or a therapeutic indication is selected from the group comprising graft versus host and host versus graft reactions, rheumatoid arthritis, multiple sclerosis, amyotrophic lateral sclerosis, lupus erythematosus, inflammatory bowel disease, and psoriasis.

14. A process for the manufacture of a white crystalline polymorph A of the Ca salt of a compound according to formula I or a solvate and/or a hydrate thereof as defined in any of embodiments 1 to 8, which process comprises the steps of Providing a Ca-Vidofludimus or a solvate and/or a hydrate thereof, preferably a crystalline polymorph of the Ca salt of vidofludimus or a solvate and/or a hydrate thereof, washing the calcium salt of Calcium-vidofludimus or a solvate and/or a hydrate thereof with the an aprotic organic solvent preferably selected from the group comprising DMF, DMSO, NMP, THF, Acetone, Dioxane, 2-Methyl-THF or (Methanol/CH2Cl2 (1:3)), preferably acetone, and slurring the isolated Calcium-vidofludimus or a solvate and/or a hydrate thereof obtained in an alcoholic solvent and adding water to the slurry.

15. A process for the manufacture of a white crystalline polymorph A of the Ca salt of a compound according to formula I or a solvate and/or a hydrate thereof as defined in any of embodiments 1 to 8, which process comprises the steps of
    a) adding to a mixture of calcium hydroxide and free acid of a compound according to formula I or a solvate and/or a hydrate thereof an organic solvent and water
    b) stirring the suspension obtained in step a) until a solution is obtained,
    c) at least partially evaporating said organic solvent and water to obtain a suspension of the calcium salt of a compound according to formula I or a solvate and/or a hydrate thereof
    d) adding an aprotic organic solvent, fully mixable with water to said suspension of the calcium salt of a compound according to formula I or a solvate and/or a hydrate thereof obtained in step c)
    e) stirring the suspension obtained in step d),
    f) recovering the calcium salt of a compound according to formula I or a solvate and/or a hydrate thereof from the mixture obtained in step e), and
    g) washing the calcium salt of a compound according to formula I or a solvate and/or a hydrate thereof obtained in step f) with the aprotic organic solvent mentioned in step d).
    h) slurring the isolated calcium salt a compound according to formula I or a solvate and/or a hydrate thereof obtained in step g) in an alcoholic solvent at 15-80° C.
    i) adding water to the slurry obtained in step h) at 15-85° C.
    j) recovering the calcium salt of a compound according to formula I or a solvate and/or a hydrate thereof from the mixture obtained in step e), and
    k) washing the calcium salt of a compound according to formula I or a solvate and/or a hydrate thereof obtained in step j) with the aprotic organic solvent mentioned in step d).
16. A process for the manufacture of a crystalline polymorph according to embodiment 14 or 15 wherein after step g) and step k) a drying step is added, and optionally subsequently a milling step and optionally subsequently a recrystallization step is added.
17. A process for the manufacture of a crystalline polymorph according to any of embodiments 14 to 16 wherein after step b) and before step c) the solution is filtered and then the filter is washed with said organic solvent.
18. A process for the manufacture of a crystalline polymorph according to any of embodiments 14 to 17 wherein the suspension of step a) is heated to 25-30° C.
19. A process for the manufacture of a crystalline polymorph according to any of embodiments 14 to 18 wherein the suspension of step e) is heated to 15-25° C.
20. A process for the manufacture of a crystalline polymorph according to any of embodiments 14 to 19 wherein said organic solvent is selected from the group comprising maybe selected from the group comprising THF, 2-Methyl-THF, Dioxane.
21. A process for the manufacture of a crystalline polymorph according to any of embodiments 14 to 20 wherein said aprotic organic solvent is selected from the group comprising DMF, DMSO, NMP, THF, Acetone, Dioxane, 2-Methyl-THF or (Methanol/CH2Cl2 (1:3)).
22. A white crystalline polymorph A of the Ca salt of a compound according to formula I or a solvate and/or a hydrate thereof with a molar ratio of a compound according to formula I to calcium of 2±0.3 obtainable by a process according to any of embodiments 14 to 21.

FIGURE DESCRIPTION

FIG. 1: PXRD of Polymorph A of Ca vidofludimus

FIG. 2: Raman spectrum of Polymorph A of Ca vidofludimus

Figure 3A:
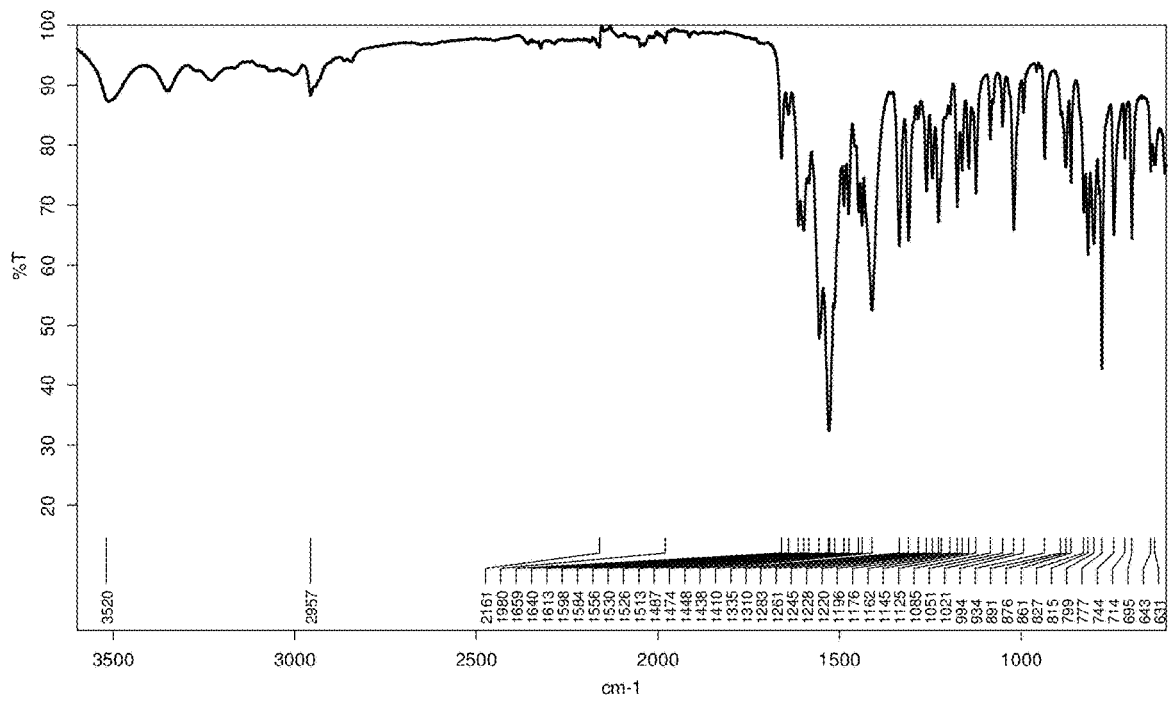

FIG. 3a: IR spectrum of Polymorph A of Ca vidofludimus, complete region.

Figure 3B:
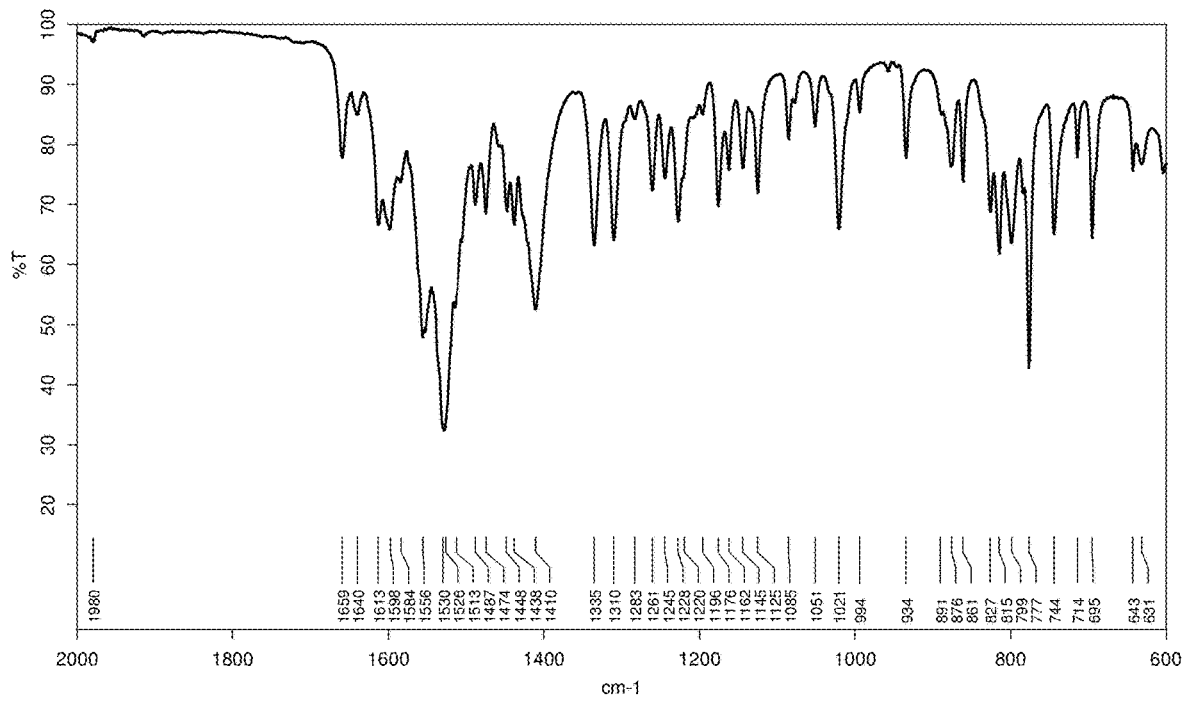

FIG. 3b: IR spectrum of Polymorph A of Ca vidofludimus, fingerprint region.

FIG. 4: $^1$H-NMR spectrum of Polymorph A of Ca vidofludimus.

Figure 5:
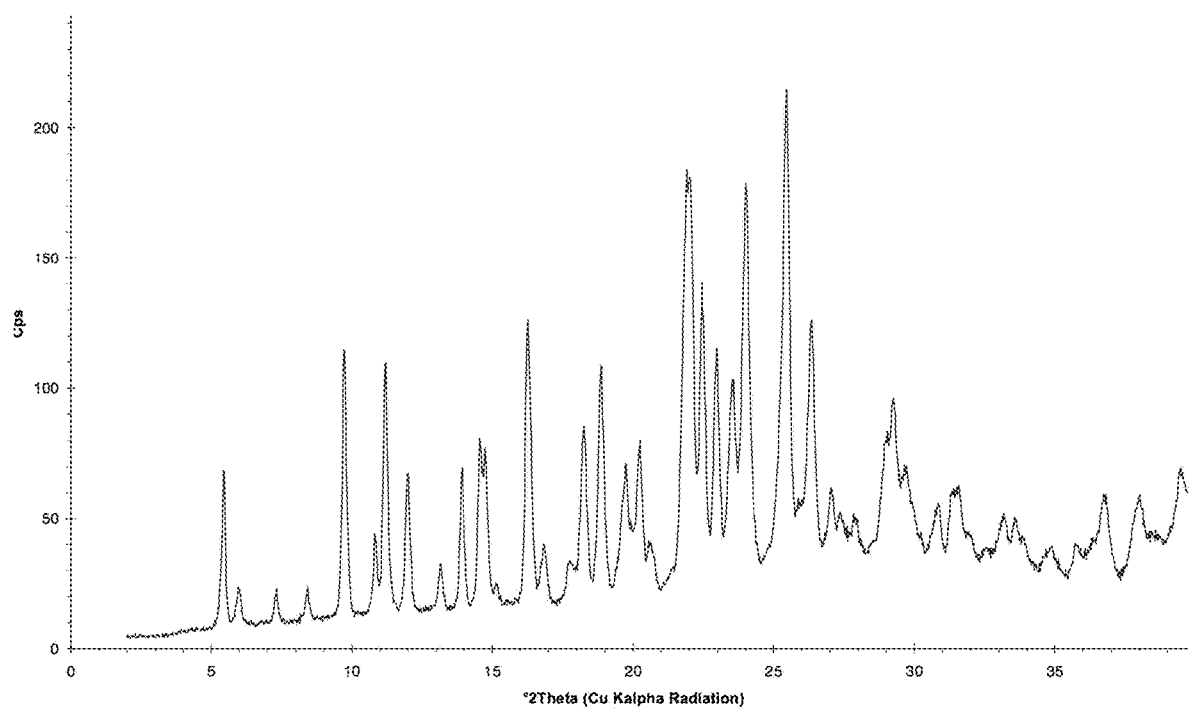

FIG. 5: PXRD of Polymorph C of the Ca salt of a compound according to formula I

Figure 6:
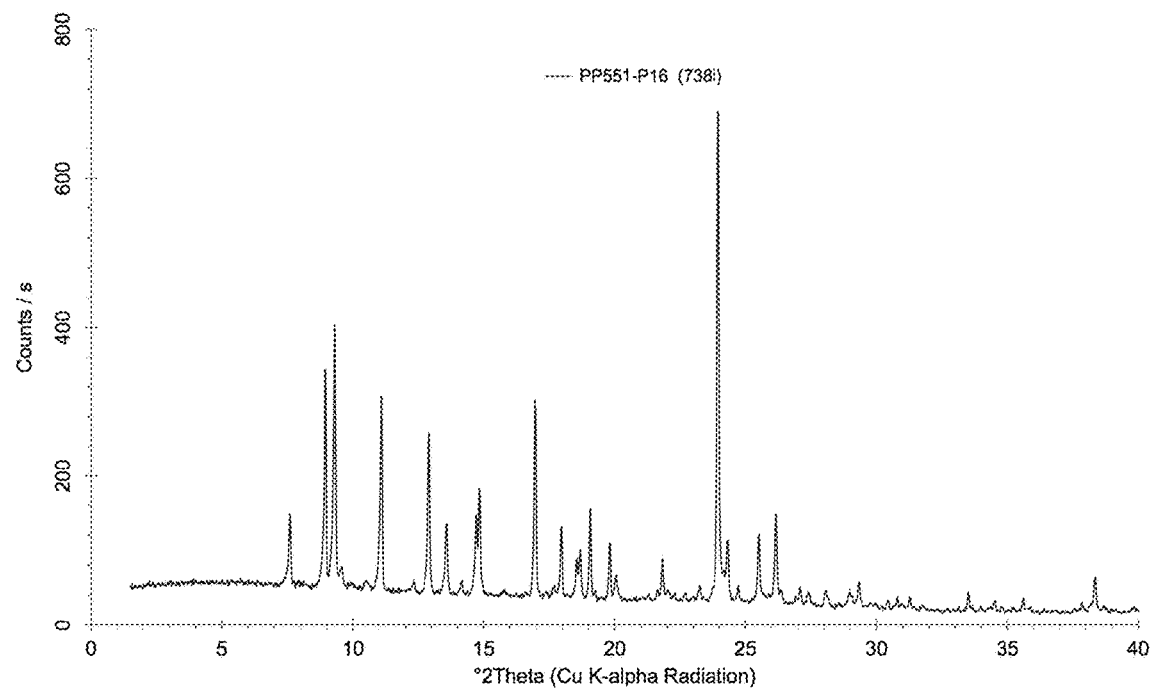

FIG. 6 PXRD of Polymorph B of the Ca salt of a compound according to formula I

EXAMPLES

Example 1

The compounds of formula (I) may be obtained via various methods, including the method described in JP-A-50-121428. In particular the two following methods of synthesis are used.

Method 1: In a first step the cycloalkene-1,2-dicarboxic acids can be obtained from the corresponding α,α'-dibromo alkanedicarboxylic acids as described by R. N. Mc Donald and R. R. Reitz, J. Org. Chem. 37, (1972) 2418-2422. Cyclopentene-1,2-dicarboxylic acid can also be obtained in large amounts from pimelic acid [D. C. Owsley and J. J. Bloomfield, Org. Prep. Proc. Int. 3, (1971) 61-70; R. Willstatter, J. Chem. Soc. (1926), 655-663].

Dicarboxylic acids substituted in or on the ring system can be synthesized in general via the cyanhydrine synthesis [Shwu-Jiüan Lee et. al., Bull. Inst. Chem. Academia Sinica Number 40, (1993), 1-10 or B. R. Baker at al., J. Org. Chem. 13, 1948, 123-133; and B. R. Baker at al., J. Org. Chem. 12, 1947, 328-332; L. A. Paquette et. al., J. Am. Chem. Soc. 97, (1975), 6124-6134].

The dicarboxylic acids can then be converted into the corresponding acid anhydrides by reacting them with acetic acid anhydride [P. Singh and S. M. Weinreb, Tetrahedron 32, (1976), 2379-2380].

Other methods for preparing different acid anhydrides of formula (II) are described in V. A. Montero at al., J. Org. Chem. 54, (1989), 3664-3667; P. ten Haken, J. Heterocycl. Chem. 7, (1970), 1211-1213; K. Alder, H. Holzrichter, J. Lieb. Annalen d. Chem. 524, (1936), 145-180; K. Alder, E. Windemuth, J. Lieb. Annalen d. Chem. 543, (1940), 56-78; and W. Flaig, J. Lieb. Annalen d. Chem. 568, (1950), 1-33.

These anhydrides may then be reacted with the corresponding amines to the desired amides of formula (I). This reaction can be carried out either by use of the reaction conditions as described in J. V. de Julian Ortiz et al., J. Med.

Chem. 42, (1999), 3308 (designated route A in Example 1) or by use of 4-dimethylamino pyridine (designated route B in Example 1).

Method 2: The amides of formula (I) can also be synthesized by reacting an amine of the formula (IV) with an arylboronic-acid of the general formula (V) [M. P. Winters, Tetrahedron Lett., 39, (1998), 2933-2936].

Biarylaniline can be synthesized in general via the palladium coupling [G. W. Kabalka et al., Chem. Commun., (2001), 775; A. Demeter, Tetrahedron Lett. 38; (1997), 5219-5222; V. Snieckus, Chem. Commun. 22, (1999), 2259-2260].

Method 3: The amides of formula (I) can also be synthesized by reacting an halogen derivative of the formula (VI) with an arylboronic acid of the general formula (VII) [N. E. Leadbeater, S. M. Resouly, Tetrahedron, 55, 1999, 11889-11894].

Example 2

Experimental/Instrument Settings $^1$H-NMR: $^1$H-NMR spectra were recorded using a Bruker DPX300 spectrometer with a proton frequency of 300.13 MHz, a 30° excitation pulse, and a recycle delay of 1 s. 16 scans were accumulated, D2O; MeOD or d6-DMSO was used as the solvent.

DSC: Differential scanning calorimetry was carried out with a Perkin Elmer DSC-7 instrument (closed gold sample pan under $N_2$ atmosphere). The sample are heated up to the melting point at a rate of 10 K/min), then cooled down (cooling rate 200 K/min) and afterwards heated up again at a rate of 10 K/min.

DVS (SMS): Surface Measurement Systems Ltd. DVS-1 water vapour sorption analyzer. The sample is placed on a platinum sample pan and allowed to equilibrate at a given relative humidity (r.h.), usually 50% r.h. Then, a pre-defined humidity program was started with a scanning rate of 5% r.h. change per hour. First step: from 50% r.h. to 0% r.h. (in case of a possibly hydrate as starting material 50 to 95% r.h.), second step: from 0% to 95% r.h. (in case of a possibly hydrate as starting material 95 to 0% r.h.)

FT-Raman spectroscopy: FT-Raman spectra were recorded on a Bruker RFS 100 FT-Raman system with a near infrared Nd:YAG laser operating at 1064 nm and a liquid nitrogen-cooled germanium detector. For each sample, a minimum of 64 scans with a resolution of 2 cm$^{-1}$ were accumulated. 300 mW nominal laser power was used. The FT-Raman data are shown in the region between 3500 to 100 cm$^{-1}$. Below 100 cm$^{-1}$ the data are unreliable due to the Rayleigh filter cut-off.

Optical Microscopy: Leitz Orthoplan 110680 microscope equipped with a Leica DFC280 camera and IM50 v.5 image-capturing software. Images were recorded with or without crossed polarizers and with 4×, 10×, or 25× magnification.

Powder X-ray diffraction: Bruker D8; Copper $K_\alpha$ radiation, 40 kV/40 mA; LynxEye detector, 0.02° 2Θ step size, 37 s step time. Sample preparation: The samples were generally measured without any special treatment other than the application of slight pressure to get a flat surface. Silicon single crystal sample holders were used (0.1, 0.5 or 1 mm deep). The samples were rotated during the measurement.

Raman microscopy: Renishaw inVia Reflex Raman System. Stabilized diode laser with 785 nm excitation and an NIR enhanced Peltier-cooled CCD camera as the detector. Measurements were carried out with a long working distance 20× objective. Wavenumber range 2000-100 cm$^{-1}$, 10 s detection time, three accumulations per spectrum.

Solvents: For all experiments, Fluka, Merck or ABCR analytical grade solvents were used.

TG-FTIR: Thermogravimetric measurements were carried out with a Netzsch Thermo-Microbalance TG 209 coupled to a Bruker FTIR Spectrometer Vector 22 or IFS 28 (sample pans with a pinhole, N2 atmosphere, heating rate 10° C./min, range 25° C. to 350° C.).

Example 3

Inhibition Assay of DHODH Activity

The standard assay mixture contained 50 µM decyclo ubichinone, 100 µM dihydroorotate, 60 µM 2,6-dichloroindophenol, as well as 20 mU DHODH. The volume activity of the recombinant enzyme used was 30 U/ml. Measurements were conducted in 50 mM TrisHCl (150 mM KCl, 0.1% Triton X-100, pH 8.0) at 30° C. in a final volume of 1 ml. The components were mixed, and the reaction was started by adding dihydroorotate. The course of reaction was followed by spectrophotometrically measuring the decrease in absorption at 600 nm for 2 min.

Inhibitory studies were conducted in a standard assay with additional variable amounts of inhibitor. For the determination of the IC$_{50}$ values (concentration of inhibitor required for 50% inhibition) at least five different inhibitor concentrations were applied.

These investigations were carried out with recombinant human as well as with recombinant murine DHODH provided by Prof. M. Löffler, Marburg, Germany [M. Löffler, Chem. Biol. Interact. 124, (2000), 61-76].

As a reference the active metabolite of leflunomide A77-1726 (Compound 12) was used [J. Jöckel et. al. Biochemical Pharmacology 56 (1998), 1053-1060].

The results of the inhibition assay are shown in the above Table 1 of said publication of Jöckel et. al. It is evident from the comparison of the IC$_{50}$-values that the compounds used for the preparation of the salts according to the present invention not only have a comparable or even better inhibitory activity on the human enzyme than the active metabolite of leflunomide but also a higher specifity for the human enzyme.

Example 4

Proliferation Assay of Human T-Cells

Human peripheral blood mononuclear cells (PBMC) were obtained from healthy volunteers and transferred to RPMI1640 cell culture medium containing 10% dialyzed fetal calf serum. 80.000 cells per well were pipetted into a 96-well plate and phytohemagglutinin (PHA) was added in phosphate buffered saline to a final concentration of 20 µg/ml to stimulate T-cell proliferation. Vidofludimus was added in dimethyl sulfoxide (DMSO, final concentration: 0.1 Vol %) to final concentrations ranging from 20 nM to 50 µM. After incubation for 48 hours, cell proliferation was quantified using the "cell proliferation ELISA BrdU" (Roche) according to the manufacturer's instructions. Half maximal inhibition (IC$_{50}$) was calculated using a 4-parameter sigmoidal curve fit. T-cell proliferation was inhibited by Vidofludimus with an IC$_{50}$ of 4.1 µM.

Example 5

Preparation of the Calcium Salts

The synthesis of the calcium salts of compounds of formula (I) is described in detail in WO 2012/001148, which is incorporated herein by reference.

In addition, the powder X-ray diffraction shown in FIG. 5 show that crystalline material was obtained, however with a pattern different from that of the free acid (see FIG. 6). With light microscopy the crystals were visualized (FIG. 4), DSC (differential scanning calorimetry) demonstrated a melting point of about 155° C. (indicating a melting of a solvate and of a non-solvated form), TG-FTIR (thermogravimetric analyzer-coupled Fourier-Transform Infrared) indicates that probably a methanol solvate and a hydrate were formed and dynamic vapor sorption revealed desolvation followed by 0.3% water uptake at about 85% r.h. and 0.4% water uptake at 95% r.h. (not reversible).

Example 6

Synthesis of the Polymorph A

Polymorph A of vidofludimus is produced as follows:
a) adding to a mixture of calcium hydroxide and free acid of a compound according to formula I or a solvate and/or a hydrate thereof an organic solvent and water
b) stirring the suspension obtained in step a) until a solution is obtained,
c) at least partially evaporating said organic solvent and water to obtain a suspension of the calcium salt of a compound according to formula I or a solvate and/or a hydrate thereof)
d) adding acetone, fully mixable with water to said suspension of the calcium salt of a compound according to formula I or a solvate and/or a hydrate thereof obtained in step c)
e) stirring the suspension obtained in step d),
f) recovering the calcium salt of a compound according to formula I or a solvate and/or a hydrate thereof from the mixture obtained in step e), and
g) washing the calcium salt of a compound according to formula I or a solvate and/or a hydrate thereof obtained in step f) with the solvent mentioned in step d).
h) slurring the isolated calcium salt a compound according to formula I or a solvate and/or a hydrate thereof obtained in step g) in an alcoholic solvent at 15-80° C.
i) adding water to the slurry obtained in step h) at 15-85° C.
j) recovering the calcium salt of a compound according to formula I or a solvate and/or a hydrate thereof from the mixture obtained in step e), and
k) washing the calcium salt of a compound according to formula I or a solvate and/or a hydrate thereof obtained in step j) with the aprotic organic solvent mentioned in step d).

Example 7

Determination of the Bioavailability

Oral bioavailabilies of the Calcium salt and the free acid of Vidofludimus were compared in male Wistar rats. The free acid or the Calcium salt was filled into gelatine capsules and the animals received a single administration at a dose level of approximately 10 mg free acid equivalents per kilogram body weight.

Four male Wistar rats (body weight range: 250-275 g) per group were treated with either Vidofludimus free acid or its Calcium salt. The capsules were administered into the oesophagus of the animals using an application device. Venous blood samples were taken from the animals under isoflurane anaesthesia at the following time points after administration: 30 min; 1 h; 2 h; 4 h; 6 h; 8 h; 24 h; 28 h; 32 h and 48 h. Coagulation was inhibited using Na-heparin and plasma was generated by centrifugation of the blood samples. Plasma samples were analyzed for Vidofludimus by LC-MS/MS and pharmacokinetic parameters were calculated according to the mixed log linear trapezoidal method.

To examine the potassium salt, six female Lewis rats (body weight ca. 200 g) were treated with either Vidofludimus free acid or its potassium salt at a dose level of 30 mg/kg (free acid equivalents). The compounds were formulated in 0.5% methylcellulose in phosphate buffered saline and the animals were treated by oral gavage. Venous blood samples were taken from the animals under isoflurane anaesthesia at the following time points after administration: 30 min; 1 h; 2 h; 4 h; 8 h; 26 h; 33 h; 48 h and 72 h. Coagulation was inhibited using Na-heparin and plasma was generated by centrifugation of the blood samples. Plasma samples were analyzed for Vidofludimus by LC-MS/MS and pharmacokinetic parameters (AUC) were calculated according to the linear trapezoidal rule method.

Oral bioavailabilies of the salts were evaluated by comparing the areas under the plasma-concentration-time-curves (AUCs) and the maximally attained plasma concentrations (Cmax values) of Vidofludimus after administration of the salt with those observed after administration of the free acid. These ratios are shown in Table 2.

TABLE 2

Comparison of PK parameters after oral application of Vidofludimus to rats

| Compound | $AUC_{inf}/AUC_{inf,\,free\,acid}$ | $C_{max}/C_{max,\,free\,acid}$ |
|---|---|---|
| Vidofludimus free acid | 1 | 1 |
| Potassium salt | 0.96 | 1.09 |
| Calcium salt | 1.72 | 1.67 |

Example 8

The previous GMP-batch of the drug substance vidofludimus calcium (IM90838; batch RL01L156A1), used in phase I studies, was manufactured from the intermediate vidofludimus (VIDO-05; SC12267) at the same facility as the current batch, i.e. Patheon DPx Fine Chemicals Regensburg GmbH—ResCom®, Regensburg, Germany. The intermediate vidofludimus used had been manufactured by Cambrex Karlskoga AB, Karlskoga, Sweden.

As the drug substance vidofludimus calcium generally incorporated the solvent tetrahydrofuran (THF) at levels of approx. 6,000 to 10,000 ppm the last step of the manufacturing process was optimised in order to reduce the THF level:

Crude vidofludimus calcium was treated with ethanol, forming an intermediate ethanol solvate which upon treatment with water gives the required polymorph of vidofludimus calcium as dihydrate. In the final drug substance ethanol is retained at levels of approx. 2,000 to 6,000 ppm which is acceptable. The process is described in section 2.1.S.2.2.

Results from the preliminary laboratory process are summarised below. Laboratory scale batches of approx. 20 g vidofludimus (VIDO-5) were transferred to vidofludimus calcium by the process described in section 3.2.S.2.2. Analytical results are summarised in Table 1.

TABLE 1

Analytical results for laboratory batches of vidofludimus calcium (IM90838)

| Batch no. | | JC3794 | JC3800 | JC3803 |
|---|---|---|---|---|
| Test | Specification | Analytical Results | | |
| Appearance | White solid | White solid | White solid | White solid |
| Identity | | | | |
| 1H-NMR | Conforms with | Conforms | Conforms | Conforms |
| FTIR | reference | Conforms | Conforms | Conforms |
| Assay VIDO-06 (IM90838; (HPLC) | 98-102% | Not determined | 100% | 100.5% |
| Assay calcium (Titration) | 4.9-5.9% (w/w) | 5.2% | 5.1% | 5.3% |
| Impurities (% w/w) | | | | |
| SC12219 [1] | ≤0.004% | n.d. | n.d. | n.d. |
| SC44107 [2] | ≤0.15% | n.d. | n.d. | n.d. |
| Single unknown impurities [3] | ≤0.1% | <0.05% (RRT 0.92) | <0.05% (RRT 0.68) <0.05% (RRT 0.92) | <0.05% (RRT 0.73) <0.05% (RRT 0.92) |
| Total impurities | ≤0.5% | 0.040% | 0.045% | 0.07% |
| Residual solvents (HS-GC) | | | | |
| THF | ≤720 ppm | 210 ppm | 42 ppm | 89 ppm |
| Acetone | ≤5,000 ppm | n.d. | 117 ppm | 14 ppm |
| Ethanol | ≤5,000 ppm | 4,777 ppm | 2,361 ppm | 4,038 ppm |
| Total heavy metals [4] | | n. det. [4] | n. det. [4] | n. det. [4] |
| Water content (KF) | <5% (w/w) | 4.6% | 5.1% | 4.8% |
| Melting point (DSC) | Report | 171.5° C. | 168.3° C. | 166.2° C. | n.d.: not detected
[1] SC12219 (VIDO-03; RRT 0.77,
[2] SC44107: RRT 0.13,
[3] report >0.05%,
[4] Not determined (n. det.) as not relevant; total heavy metals were determined to be ≤20 ppm in vidofludimus and no additional metal impurities are expected in the laboratory batches.

It can be noted that the laboratory batches of vidofludimus calcium contain THF below the guideline limit of NMT 720 ppm; however the ethanol content is determined up to approx. 5,000 ppm. No change in assay or in the impurity level is observed.

The invention claimed is:

1. A crystalline polymorph A of a hydrate of the Ca salt of a compound according to formula I,

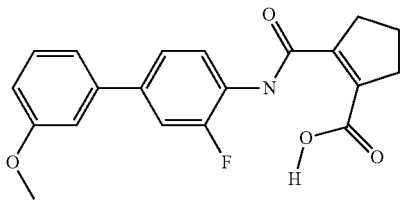

Formula I wherein the crystalline polymorph A is characterized by an X-ray powder diffraction pattern having characteristic peaks expressed in degrees 2theta at ±0.2 of the values shown below:

2theta=5.91°, 9.64°, 16.78°, 17.81°, 19.81°, and 25.41°, and wherein a molar ratio of the compound according to formula I to calcium to water is 2±0.3 to 1 to 2.

2. The crystalline polymorph A according to claim 1, having characteristic necks of 2theta at ±0.2 of the values shown below:

| Angle 2-Theta ° | d value Angstrom | Intensity |
|---|---|---|
| 5.91 | 14.95 | vs |
| 6.83 | 12.93 | vw |
| 9.64 | 9.17 | w |
| 11.33 | 7.80 | w |
| 11.82 | 7.48 | w |
| 12.98 | 6.81 | vw |
| 13.70 | 6.46 | vw |
| 14.27 | 6.20 | vw |
| 15.04 | 5.89 | w |
| 15.44 | 5.73 | vw |
| 16.78 | 5.28 | s |
| 17.81 | 4.98 | m |
| 18.25 | 4.86 | w |
| 18.58 | 4.77 | vw |
| 19.39 | 4.57 | w |
| 19.81 | 4.48 | w |
| 20.53 | 4.32 | vw |
| 21.26 | 4.18 | vw |
| 22.63 | 3.93 | vw |
| 23.16 | 3.84 | vw |
| 23.96 | 3.71 | w |
| 24.73 | 3.60 | vw |
| 25.41 | 3.50 | s |
| 26.12 | 3.41 | w |
| 26.44 | 3.37 | w |
| 27.25 | 3.27 | w |
| 27.55 | 3.24 | w |
| 28.45 | 3.13 | w |
| 28.91 | 3.09 | vw |
| 29.29 | 3.05 | w |
| 29.89 | 2.99 | w |
| 30.77 | 2.90 | w |
| 31.22 | 2.86 | vw |
| 31.60 | 2.83 | w |
| 32.13 | 2.78 | w |
| 33.25 | 2.69 | vw |

| Angle<br>2-Theta ° | d value<br>Angstrom | Intensity |
|---|---|---|
| 33.98 | 2.64 | w |
| 34.48 | 2.60 | w |
| 35.12 | 2.55 | vw. |

3. The crystalline polymorph A according to claim 1, which is characterized by an FT Raman absorption spectrum having the following characteristic peaks pattern expressed in cm$^{-1}$ 1664, 1624, 1617, 1532, 1449, and 1338.

4. The crystalline polymorph A according to claim 1, which is characterized by an IR absorption spectrum having a characteristic peaks pattern expressed in cm$^{-1}$ 1980, 1659, 1584, 1335, and 1145.

5. The crystalline polymorph A according to claim 1, which is characterized by an $^1$H-NMR spectrum in DMSO having a characteristic peaks pattern expressed in ppm, 15.2, 8.3, 7.6, 7.5, 7.4, 7.2, 6.8, 3.8, 2.7, and 1.6.

6. A pharmaceutical formulation comprising the crystalline polymorph A according to claim 1 and a pharmaceutically acceptable excipient.

7. The pharmaceutical formulation according to claim 6, wherein the crystalline polymorph A has a THF content of less than 720 ppm.

8. A method for treating a disease selected from the group consisting of graft versus host and host versus graft reactions, rheumatoid arthritis, inflammatory bowel disease, and multiple sclerosis, comprising administering to a subject in need thereof an effective amount of the-crystalline polymorph A according to claim 1.

9. A process for the manufacture of a crystalline polymorph A, which process comprises the steps of
providing a Calcium-Vidofludimus or a hydrate thereof,
washing and isolating the Calcium-vidofludimus or a hydrate thereof with an aprotic organic solvent, and
slurring the isolated Calcium-vidofludimus or a hydrate thereof obtained in an alcoholic solvent and adding water to the slurry.

10. A process for the manufacture of the crystalline polymorph A in claim 1, which process comprises the steps of
a) adding to a mixture of calcium hydroxide and a free acid form of a compound according to formula I or a hydrate thereof, an organic solvent and water, to obtain a suspension,
b) stirring the suspension obtained in step a) until a solution is obtained,
c) at least partially evaporating said organic solvent and water to obtain a suspension of the calcium salt of a compound according to formula I or a hydrate thereof
d) adding an aprotic organic solvent, fully mixable with water to said suspension of the calcium salt of a compound according to formula I or a hydrate thereof obtained in step c)
e) stirring the suspension obtained in step d),
f) recovering the calcium salt of a compound according to formula I or a hydrate thereof from the mixture obtained in step e), and
g) washing and isolating the calcium salt of a compound according to formula I or a hydrate thereof obtained in step f) with the aprotic organic solvent mentioned in step d),
h) slurring the isolated calcium salt a compound according to formula I or a hydrate thereof obtained in step g) in an alcoholic solvent at 15-80° C.,
i) adding water to the slurry obtained in step h) at 15-85° C.
j) recovering the calcium salt of a compound according to formula I or a hydrate thereof from the mixture obtained in step i), and
k) washing the calcium salt of a compound according to formula I or a hydrate thereof obtained in step j) with the aprotic organic solvent mentioned in step d).

11. The process for the manufacture of the crystalline polymorph according to claim 10 wherein after step g) and step k) a drying step is added, and optionally subsequently a milling step and optionally subsequently a recrystallization step is added.

12. The process for the manufacture of the crystalline polymorph according to claim 10 wherein after step b) and before step c) the solution is filtered and then the filter is washed with said organic solvent.

13. The process for the manufacture of the crystalline polymorph according to claim 10 wherein the suspension of step a) is heated to 25-30° C.

14. The process for the manufacture of the crystalline polymorph according to claim 10 wherein the suspension of step e) is heated to 15-25° C.

15. The process for the manufacture of the crystalline polymorph according to claim 9 wherein said organic solvent is selected from the group consisting of DMF, DMSO, NMP, THF, Acetone, Dioxane, 2-Methyl-THF and (Methanol/CH2Cl2 (1:3)).

16. A crystalline polymorph A of a hydrate of the Ca salt of a compound according to formula I with a molar ratio of a compound according to formula I to calcium to water of 2±0.3 to 1 to 2 obtainable by a process according to claim 9.

* * * * *

UNITED STATES PATENT AND TRADEMARK OFFICE
CERTIFICATE OF CORRECTION

| | | |
|---|---|---|
| PATENT NO. | : 12,037,305 B2 | Page 1 of 2 |
| APPLICATION NO. | : 16/981122 | |
| DATED | : July 16, 2024 | |
| INVENTOR(S) | : Daniel Vitt et al. | |

It is certified that error appears in the above-identified patent and that said Letters Patent is hereby corrected as shown below:

On the Title Page

Item (73), in the Assignee, "Grafelfing (DE)" should read --Gräfelfing (DE)--.

Item (57), in the Abstract, Line 11, "19.81°, 25.41°" should read --19.81°, and 25.41°.--.

In the Claims

In Claim 1, Column 17, Lines 46-54, in the structure for Formula I,

" 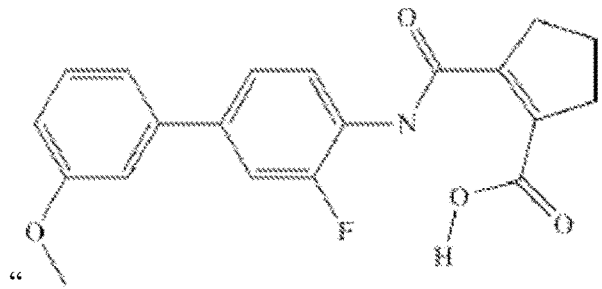 " should read

-- 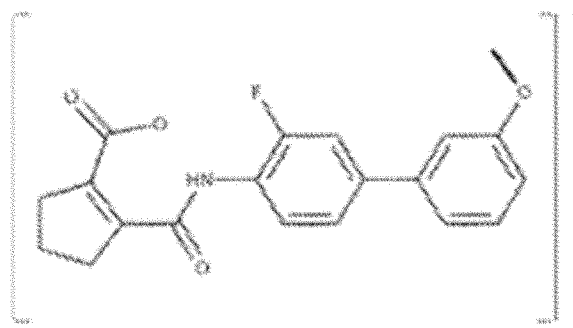 --.

In Claim 2, Column 17, Line 66, "characteristic necks" should read --characteristic peaks--.

Signed and Sealed this
Eighteenth Day of November, 2025

John A. Squires
*Director of the United States Patent and Trademark Office*

CERTIFICATE OF CORRECTION (continued)
U.S. Pat. No. 12,037,305 B2

In Claim 3, Column 19, Line 11, "characteristic peaks pattern" should read --characteristic peak pattern--.

In Claim 4, Column 19, Line 15, "characteristic peaks pattern" should read --characteristic peak pattern--.

In Claim 5, Column 19, Line 19, "characteristic peaks pattern" should read --characteristic peak pattern--.

In Claim 8, Column 19, Line 31, "the-crystalline" should read --the crystalline--.

In Claim 10, Column 20, Line 14, "calcium salt a compound" should read --calcium salt of a compound--.